US012220349B2

(12) United States Patent
Yan et al.

(10) Patent No.: US 12,220,349 B2
(45) Date of Patent: Feb. 11, 2025

(54) ULTRASONIC HANDPIECE WITH FLOATING HORN

(71) Applicant: Alcon Inc., Fribourg (CH)

(72) Inventors: John Zhongyu Yan, Irvine, CA (US); John Morgan Bourne, Irvine, CA (US); Francisco Javier Ochoa, Cudahy, CA (US)

(73) Assignee: Alcon Inc., Fribourg (CH)

( * ) Notice: Subject to any disclaimer, the term of this patent is extended or adjusted under 35 U.S.C. 154(b) by 775 days.

(21) Appl. No.: 16/779,691

(22) Filed: Feb. 3, 2020

(65) Prior Publication Data

US 2020/0246187 A1 Aug. 6, 2020

Related U.S. Application Data

(60) Provisional application No. 62/801,677, filed on Feb. 6, 2019.

(51) Int. Cl.
*A61F 9/007* (2006.01)
*A61B 17/00* (2006.01)

(52) U.S. Cl.
CPC .............. *A61F 9/00745* (2013.01); *A61B 2017/00199* (2013.01); *A61B 2017/00402* (2013.01); *A61B 2217/005* (2013.01); *A61B 2217/007* (2013.01)

(58) Field of Classification Search
CPC ..... A61F 9/00736–00763; A61B 2017/00402; A61B 2217/005; A61B 17/320068–2017/320098
See application file for complete search history.

(56) References Cited

U.S. PATENT DOCUMENTS

| 3,526,219 A | 9/1970 | Balamuth |
| 3,589,363 A | 6/1971 | Banko et al. |
| 3,601,126 A | 8/1971 | Estes |

(Continued)

FOREIGN PATENT DOCUMENTS

| AU | 2005203353 B2 | 6/2009 |
| CA | 2512806 C | 1/2012 |

(Continued)

OTHER PUBLICATIONS

Office action dated Feb. 16, 2017 issued against Chinese patent application No. 201410326391.6.

(Continued)

*Primary Examiner* — Brigid K Byrd
(74) *Attorney, Agent, or Firm* — PATTERSON + SHERIDAN, LLP (57) ABSTRACT

Systems and methods are disclosed comprising an ultrasonic handpiece having a housing, a working tip extending from the distal end of the housing, and a crystal and horn assembly positioned within the housing. The proximal end of the ultrasonic horn is free to move relative to the housing. In embodiments, the ultrasonic horn is resiliently suspended within the housing, with no rigid fixation points. The ultrasonic horn may be resiliently suspended by one or more resilient rings at the proximal end of the ultrasonic horn and by one or more resilient rings at the single nodal region of the ultrasonic horn. The ultrasonic handpiece may include a pumping module located at the proximal end of the handpiece.

19 Claims, 5 Drawing Sheets

(56) References Cited

U.S. PATENT DOCUMENTS

| | | |
|---|---|---|
| 3,693,613 A | 9/1972 | Kelman |
| 3,812,855 A | 5/1974 | Banko |
| 3,812,858 A | 5/1974 | Oringer |
| 3,857,387 A | 12/1974 | Shock |
| 3,902,495 A | 9/1975 | Weiss et al. |
| 3,930,505 A | 1/1976 | Wallach |
| 3,942,519 A | 3/1976 | Shock |
| 3,952,732 A | 4/1976 | Shock |
| 3,956,826 A | 5/1976 | Perdreaux, Jr. |
| 3,964,487 A | 6/1976 | Judson |
| 3,990,452 A | 11/1976 | Murry et al. |
| 4,024,467 A | 5/1977 | Andrews et al. |
| 4,024,866 A | 5/1977 | Wallach |
| 4,114,623 A | 9/1978 | Meinke et al. |
| 4,126,137 A | 11/1978 | Archibald |
| 4,156,187 A | 5/1979 | Murry et al. |
| 4,168,707 A | 9/1979 | Douvas et al. |
| 4,184,510 A | 1/1980 | Murry et al. |
| 4,223,676 A | 9/1980 | Wuchinich et al. |
| 4,246,902 A | 1/1981 | Martinez |
| 4,248,232 A | 2/1981 | Engelbrecht et al. |
| 4,406,284 A | 9/1983 | Banko |
| 4,417,578 A | 11/1983 | Banko |
| 4,493,694 A | 1/1985 | Wuchinich |
| 4,496,342 A | 1/1985 | Banko |
| 4,504,264 A | 3/1985 | Kelman |
| 4,508,532 A | 4/1985 | Drews et al. |
| 4,515,583 A | 5/1985 | Sorich |
| 4,589,415 A | 5/1986 | Haaga |
| 4,590,935 A | 5/1986 | Ranalli |
| 4,609,368 A | 9/1986 | Dotson, Jr. |
| 4,643,717 A * | 2/1987 | Cook ................ A61F 9/00745 604/48 |
| 4,651,280 A | 3/1987 | Chang et al. |
| 4,658,819 A | 4/1987 | Harris et al. |
| 4,705,500 A | 11/1987 | Reimels et al. |
| 4,712,544 A | 12/1987 | Ensslin |
| 4,739,759 A | 4/1988 | Rexroth et al. |
| 4,750,488 A | 6/1988 | Wuchinich et al. |
| 4,770,654 A | 9/1988 | Rogers et al. |
| 4,793,346 A | 12/1988 | Mindich |
| 4,827,911 A | 5/1989 | Broadwin et al. |
| 4,869,715 A | 9/1989 | Sherburne |
| 4,922,902 A | 5/1990 | Wuchinich et al. |
| 4,961,424 A | 10/1990 | Kubota et al. |
| 4,969,885 A | 11/1990 | Farin |
| 4,989,583 A | 2/1991 | Hood |
| 4,989,588 A | 2/1991 | Kubota et al. |
| 5,026,387 A | 6/1991 | Thomas |
| 5,116,343 A | 5/1992 | Ams et al. |
| 5,139,509 A | 8/1992 | Fischer et al. |
| 5,151,085 A | 9/1992 | Sakurai et al. |
| 5,154,694 A | 10/1992 | Kelman |
| 5,154,696 A | 10/1992 | Shearing |
| 5,160,317 A | 11/1992 | Costin |
| 5,178,605 A * | 1/1993 | Imonti ................ A61F 9/00745 604/22 |
| 5,180,363 A | 1/1993 | Idemoto et al. |
| 5,188,102 A | 2/1993 | Idemoto et al. |
| 5,205,817 A | 4/1993 | Idemoto et al. |
| 5,222,959 A | 6/1993 | Anis |
| 5,242,385 A | 9/1993 | Strukel |
| 5,279,547 A | 1/1994 | Costin |
| 5,304,115 A | 4/1994 | Pflueger et al. |
| 5,342,293 A | 8/1994 | Zanger |
| 5,359,996 A | 11/1994 | Hood |
| 5,431,664 A | 7/1995 | Ureche et al. |
| 5,453,087 A * | 9/1995 | Malinowski ........ A61F 9/00745 604/22 |
| 5,520,633 A | 5/1996 | Costin |
| 5,569,188 A | 10/1996 | Mackool |
| 5,591,127 A | 1/1997 | Barwick, Jr. et al. |
| 5,676,649 A | 10/1997 | Boukhny et al. |
| 5,695,461 A * | 12/1997 | Schaible ............ A61F 9/008 606/166 |
| 5,700,240 A | 12/1997 | Barwick, Jr. et al. |
| 5,722,945 A | 3/1998 | Anis et al. |
| 5,733,256 A | 3/1998 | Costin |
| 5,766,146 A | 6/1998 | Barwick, Jr. |
| 5,808,396 A | 9/1998 | Boukhny |
| 5,865,790 A | 2/1999 | Bair |
| 5,879,363 A * | 3/1999 | Urich ............ A61B 17/320068 606/167 |
| 6,027,515 A | 2/2000 | Cimino |
| 6,028,387 A | 2/2000 | Boukhny |
| 6,077,285 A | 6/2000 | Boukhny |
| 6,083,193 A | 7/2000 | Kadziauskas et al. |
| 6,175,180 B1 | 1/2001 | Angelini et al. |
| 6,179,808 B1 | 1/2001 | Boukhny et al. |
| 6,193,683 B1 | 2/2001 | Ludin et al. |
| 6,241,700 B1 * | 6/2001 | Leukanech ........ A61F 9/00745 604/22 |
| 6,261,283 B1 | 7/2001 | Morgan et al. |
| 6,261,297 B1 | 7/2001 | Kadziauskas et al. |
| 6,283,974 B1 | 9/2001 | Alexander |
| 6,315,755 B1 | 11/2001 | Sussman |
| 6,402,769 B1 | 6/2002 | Boukhny |
| 6,629,948 B2 | 10/2003 | Rockley et al. |
| 6,699,212 B1 | 3/2004 | Kadziauskas et al. |
| 6,780,165 B2 | 8/2004 | Kadziauskas et al. |
| 7,374,552 B2 | 5/2008 | Wuchinich |
| 7,572,242 B2 | 8/2009 | Boukhny |
| 7,645,256 B2 | 1/2010 | Boukhny |
| 7,651,490 B2 | 1/2010 | Boukhny et al. |
| 8,172,786 B2 | 5/2012 | Boukhny |
| 8,771,301 B2 | 7/2014 | Boukhny |
| 8,814,894 B2 | 8/2014 | Boukhny |
| 2001/0001123 A1 | 5/2001 | Madan |
| 2001/0011176 A1* | 8/2001 | Boukhny ............ A61F 9/00745 606/169 |
| 2003/0045887 A1 | 3/2003 | Sakurai |
| 2003/0164659 A1 | 9/2003 | Iino |
| 2004/0092800 A1 | 5/2004 | Mackool |
| 2004/0092922 A1 | 5/2004 | Kadziauskas |
| 2004/0215127 A1 | 10/2004 | Kadziauskas |
| 2006/0041200 A1 | 2/2006 | Dotter |
| 2010/0056986 A1* | 3/2010 | Allen ................ A61F 9/00745 604/22 |
| 2014/0012296 A1* | 1/2014 | Sussmen ............ A61F 9/00745 606/169 |
| 2014/0271251 A1* | 9/2014 | Bourne ............... A61F 9/00745 417/475 |
| 2020/0093507 A1* | 3/2020 | James ................ A61B 90/98 |

FOREIGN PATENT DOCUMENTS

| | | |
|---|---|---|
| CN | 2414741 Y | 1/2001 |
| CN | 203408926 U | 1/2014 |
| CN | 104161618 A | 11/2014 |
| CN | 203988626 U | 12/2014 |
| EP | 0359217 A2 | 3/1990 |
| EP | 1625836 B1 | 10/2010 |
| EP | 2243449 B1 | 10/2013 |
| JP | H09-9656 A | 1/1997 |
| JP | 2003-033364 A | 2/2003 |
| JP | 4473192 B2 | 6/2010 |
| WO | 87/05793 A1 | 10/1987 |
| WO | 92/07622 A1 | 5/1992 |
| WO | 99/45868 A1 | 9/1999 |
| WO | 01/41672 A2 | 6/2001 |
| WO | 2004/080505 A2 | 9/2004 |

OTHER PUBLICATIONS

Shuyu, "Sandwiched Piezoelectric Ultrasonic Transducers of Longitudinal-Torsional Compound Vibrational Modes", Nov. 1997, pp. 1189-1197, vol. 44, No. 6, IEEE Transactions on Ultrasonics, Ferroelectrics, and Frequency Control.

(56) References Cited

OTHER PUBLICATIONS

Tsujino, "Ultrasonic motor using a one-dimensional longitudinal-torsional vibration converter with diagonal slits", Jun. 1998, pp. 345-351, vol. 7, No. 3, Smart Materials and Structures.

* cited by examiner

ULTRASONIC HANDPIECE WITH FLOATING HORN

CROSS-REFERENCE TO RELATED APPLICATIONS

This application claims the benefit of U.S. Provisional Application Ser. No. 62/801,677 (filed on Feb. 6, 2019), the content of which is incorporated herein by reference in its entirety.

TECHNICAL FIELD

The present disclosure is directed to ultrasonic handpieces such as ultrasonic ophthalmic phacoemulsification handpieces.

BACKGROUND

Ultrasonic handpieces utilize ultrasonic vibrations to drive movement of a working tip of the handpiece in order to perform a desired action. Ultrasonic ophthalmic phacoemulsification handpieces, for example, are used in cataract surgery for removal of cataractous lenses. In such handpieces, ultrasonic vibrations drive a phacoemulsification working tip which the physician can maneuver against the cataractous lens in order to break up or emulsify the lens for removal and replacement.

Ultrasonic ophthalmic phacoemulsification handpieces in common use typically are designed not only to drive the ultrasonic working tip but also to perform additional functions, such as to facilitate supplying irrigation fluid into the eye and to facilitate aspiration of fluid and of the fragmented or emulsified lens from the eye. Parts of such ultrasonic handpieces typically include a handpiece housing, a working tip extending from the housing, components within the housing for driving vibration of the working tip, an irrigation supply line within the housing, an irrigating sleeve around the working tip for directing the irrigation fluid, and an aspiration channel through which fluid and the fragmented or emulsified lens may be removed from the eye. The handpiece may be connected to a control console by one or more electric cables and flexible tubes. The electric cable supplies power to the components for driving vibration of the working tip, while the tubes serve as conduits for the irrigation fluid supplied to the eye and for the aspirated fluid drawn from the eye.

The components within the housing for driving vibration of the working tip include an ultrasonic horn mounted within the housing and a set of piezoelectric crystals attached to the ultrasonic horn. At its distal end, the ultrasonic horn is attached to the working tip, which extends distally from the housing of the handpiece. When the piezoelectric crystals are activated through power supplied via the electric cable(s) from the control console, they cause the ultrasonic horn to vibrate, which in turn causes the working tip to vibrate. The crystal/horn assembly is suspended within the housing of the handpiece at its nodal points by inflexible mountings. The typical crystal/horn assembly has a nodal point at its proximal end and is rigidly mounted there to the housing.

There is a continued need for improved ultrasonic handpieces and associated methods of use.

SUMMARY

The present disclosure is directed to improved designs for ultrasonic handpieces and associated methods of use.

In one embodiment, an ultrasonic handpiece comprises a housing, a working tip, an ultrasonic horn, and a set of piezoelectric crystals that induce vibration of the ultrasonic horn, wherein the proximal end of the ultrasonic horn is free to move relative to the housing. The ultrasonic horn may be resiliently suspended within the housing, for example by one or more resilient rings. The ultrasonic horn may be resiliently suspended at its proximal end by one or more resilient rings, which may be positioned within an aspiration luer that is rigidly fixed to the housing at the proximal end of the housing. The ultrasonic horn may have a single nodal region located between the proximal end and the distal end of the ultrasonic horn and may be suspended at its single nodal region by one or more resilient rings. A pumping module may be located at the proximal end of the handpiece.

In another embodiment, a method of using an ultrasonic handpiece comprises activating an ultrasonic handpiece as described above and vibrating the ultrasonic horn such that the working tip is vibrated and such that the proximal end of the ultrasonic horn moves relative to the housing.

In another embodiment, a system for performing operations with an ultrasonic handpiece comprises an ultrasonic handpiece as described above, a control console for controlling operations of the ultrasonic handpiece, and at least one electrical connection between the control console and the ultrasonic handpiece.

BRIEF DESCRIPTION OF THE DRAWINGS

The accompanying drawings illustrate implementations of the devices and methods disclosed herein and, together with the description, serve to explain the principles of the present disclosure.

The accompanying drawings may be better understood by reference to the following detailed description.

DETAILED DESCRIPTION

For the purposes of promoting an understanding of the principles of the disclosure, reference will now be made to the implementations illustrated in the drawings, and specific language will be used to describe the same. It will nevertheless be understood that no limitation of the scope of the disclosure is intended. Any alterations and further modifications to the described systems, devices, instruments, methods, and any further application of the principles of the present disclosure are fully contemplated as would normally occur to one skilled in the art to which the disclosure relates. In particular, the features, components, and/or steps described with respect to one implementation may be combined with the features, components, and/or steps described with respect to other implementations of the disclosure. For simplicity, in some instances the same reference numbers are used throughout the drawings to refer to the same or like parts.

Figure 1:
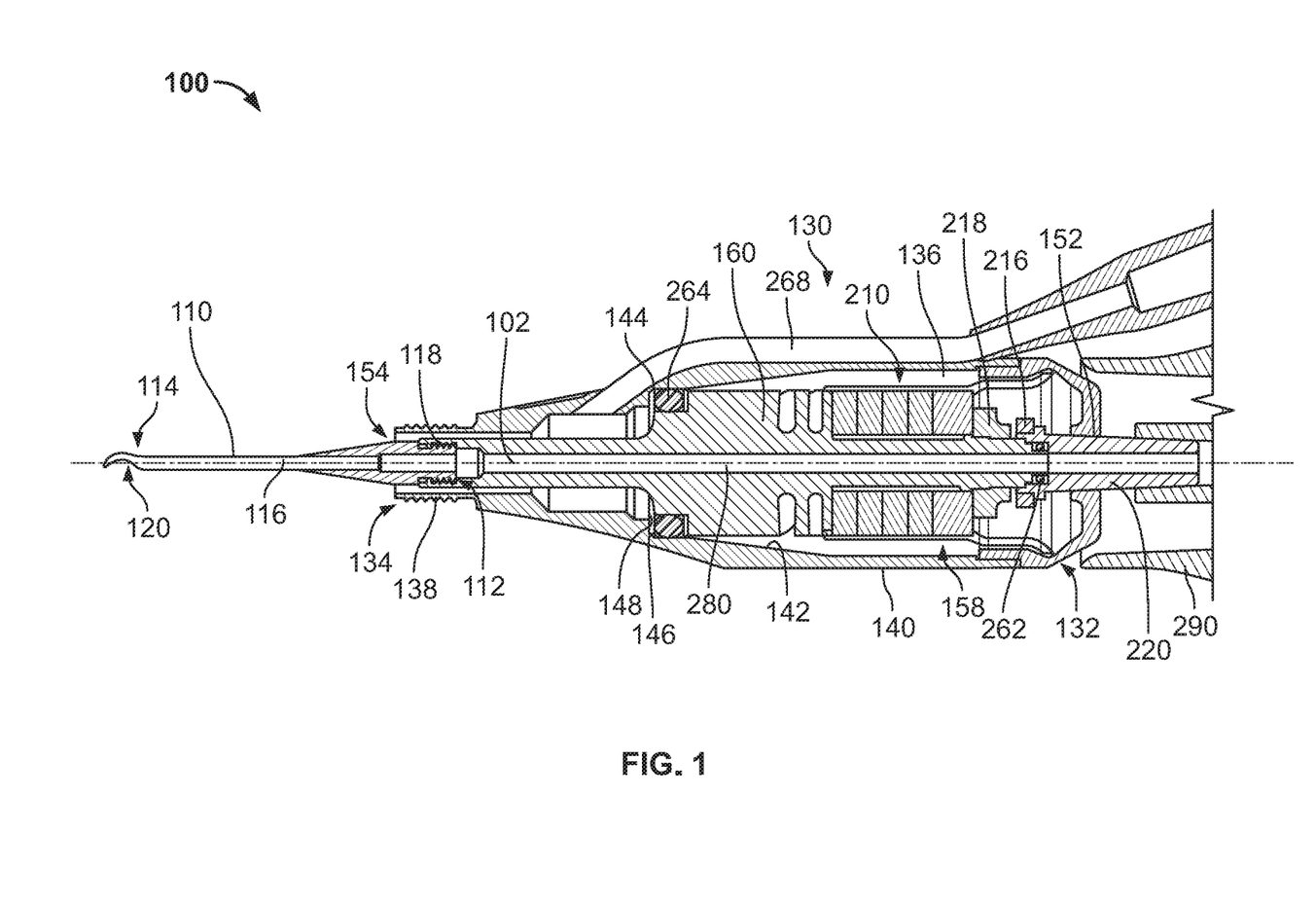
FIG. 1 shows a cross-sectional view of an example of an ultrasonic handpiece in accordance with the disclosure.
Figure 2:
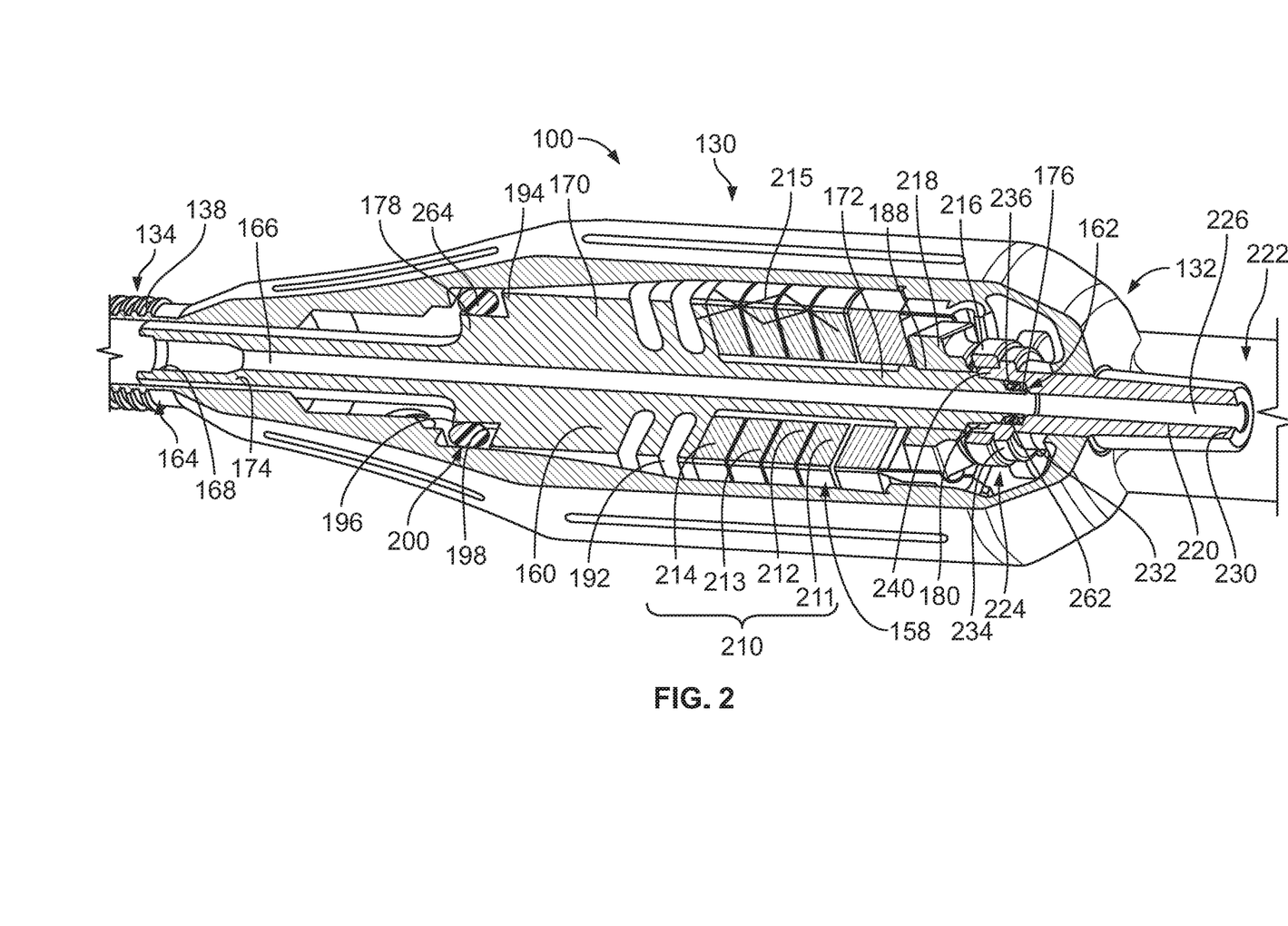
FIG. 2 shows a cut-away view of the ultrasonic handpiece of FIG. 1.

FIG. 1 shows a cross-sectional view of an example of an ultrasonic handpiece 100 in accordance with the disclosure. FIG. 2 shows a cut-away view of the ultrasonic handpiece 100 of FIG. 1.

As can be seen in FIGS. 1 and 2, ultrasonic handpiece 100 comprises a housing 130 having a proximal end 132 and a distal end 134, a working tip 110 that extends from the distal end 134 of the housing 130, and a crystal and horn assembly 158 positioned within the housing 130. The crystal and horn assembly 158 comprises an ultrasonic horn 160 and a set of piezoelectric crystals 210. The ultrasonic horn 160 has a proximal end 162 and a distal end 164, and a proximal end 112 of the working tip 110 is connected to the distal end 164 of the ultrasonic horn 160. A distal end 114 of the working tip 110 comprises a working end 120 for performing a desired operation, such as a phacoemulsification procedure in an ophthalmic phacoemulsification handpiece. In the illustrated example, the working end 120 is bent or angled.

The housing 130 is hollow and defines an internal hollow chamber 136 in which internal components of the ultrasonic handpiece 100 are housed and protected. The housing 130 has an external surface 140 that can be grasped by an operator of the ultrasonic handpiece 100, such as a surgeon. The hollow shell of the housing 130 has an internal surface 142 defining the hollow chamber 136. At its distal end 134, the housing 130 has an opening 154 through which the working tip 110 extends. At its proximal end 132, the housing has a port 152 through which an aspiration luer 220 extends.

In order to drive vibration of the working tip 110, as stated above the proximal end 112 of the working tip 110 is connected to the distal end 164 of the ultrasonic horn 160. The connection between the working tip 110 and the ultrasonic horn 160 may be made by any suitable connection. For example, the proximal end 112 of the working tip 110 may have threads 118 and the distal end 164 of the ultrasonic horn 160 may have threads 168 by which the working tip 110 may be connected to the ultrasonic horn 160.

The aspiration luer 220, the ultrasonic horn 160, and the working tip 110 are generally aligned along a longitudinal axis 102 of the ultrasonic handpiece 100. The longitudinal axis 102 extends in a longitudinal direction, and each of the aspiration luer 220, ultrasonic horn 160, and working tip 110 has a longitudinal axis that is aligned with the longitudinal axis 102 of the ultrasonic handpiece 100.

The aspiration luer 220 has a channel 226 extending longitudinally through the aspiration luer 220 from a proximal end 222 of the aspiration luer 220 to a distal end 224 of the aspiration luer 220. The ultrasonic horn 160 has a channel 166 extending longitudinally through the ultrasonic horn 160 from the proximal end 162 of the ultrasonic horn 160 to the distal end 164 of the ultrasonic horn 160. The working tip 110 has a channel 116 extending longitudinally through the working tip 110 from the proximal end 112 of the working tip 110 to the distal end 114 of the working tip 110. The channel 226 of the aspiration luer 220 is open at the proximal end 222 of the aspiration luer 220 to provide an aspiration passageway through the housing 130. As described further below, suction may be applied to the channel 226 at the proximal end 222 of the aspiration luer 220. The channels 226, 166, and 116 are all aligned and connected to form an elongated aspiration channel 280 that extends through these components. The working tip 110 has an opening at its distal end 114 which may be used for aspiration. For example, by applying suction through the aspiration channel 280 from the proximal end 222 of the aspiration luer 220, fluid and/or tissue, such as lens or other tissue fragments in a phacoemulsification procedure, may be aspirated through the opening in the distal end 114 of the working tip 110 and through the channels 226, 166, and 116.

Figure 3:
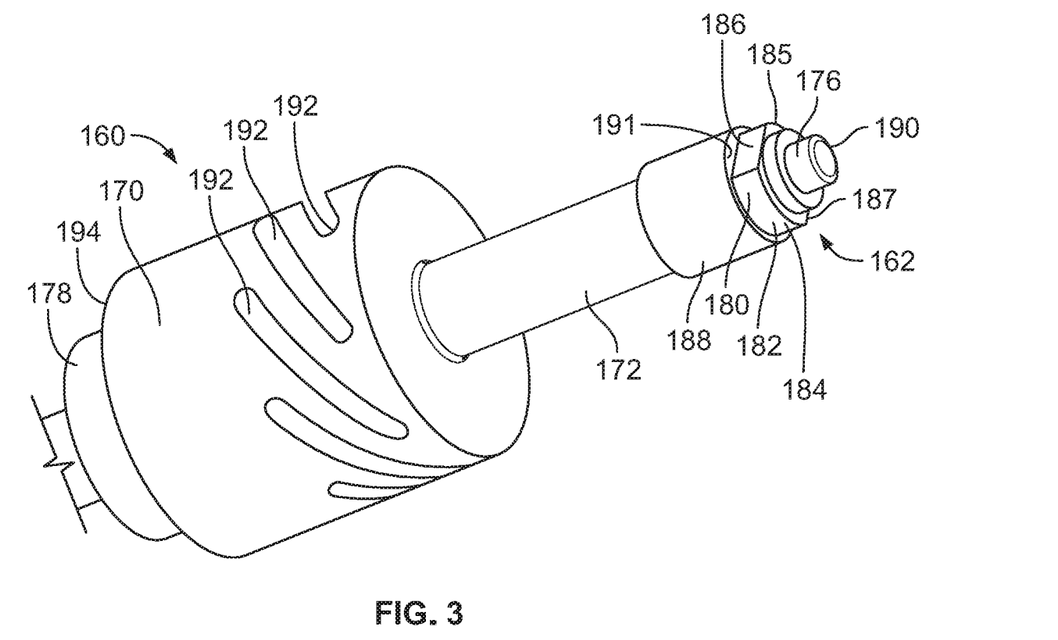
FIG. 3 shows a perspective view of the proximal end of the ultrasonic horn component of the ultrasonic handpiece of FIG. 1.

FIG. 3 shows a perspective view of the proximal end of the ultrasonic horn 160 of the ultrasonic handpiece 100 of FIG. 1. As shown in FIGS. 1-3, the ultrasonic horn 160 comprises a body 170, a proximal shaft 172, and a distal shaft 174. The proximal end 162 of the ultrasonic horn ends in a proximal end surface 190. The set of piezoelectric crystals 210 is mounted along the proximal shaft 172 of the ultrasonic horn 160. In this example, the set of piezoelectric crystals comprises four piezoelectric crystals 211, 212, 213, 214, although numerous variations are possible. In operation, as described further below, the piezoelectric crystals 211, 212, 213, 214 induce vibration of the ultrasonic horn 160.

On the distal side of the body 170, the ultrasonic horn 160 comprises a reduced-diameter portion 178 that has a smaller diameter than the body 170. The transition from the body 170 to the reduced-diameter portion forms a shoulder 194. The reduced-diameter portion 178 has an outwardly-facing surface 198 and is sized to leave a small gap between the outwardly-facing surface 198 and an inwardly-facing surface 146 of the internal surface 142 of the housing 130. In order to resiliently support the ultrasonic horn 160 in this region, a resilient elastomeric O-ring 264 is positioned between the outwardly-facing surface 198 of the ultrasonic horn 160 and the inwardly-facing surface 146 of the housing 130. As described further below, this region in which the ultrasonic horn 160 is supported by the resilient O-ring 264 between the housing 130 and the ultrasonic horn 160 is a nodal region 200 of the ultrasonic horn 160. In this region, the internal surface 142 of the housing 130 may be shaped to have a shoulder 144 and to present a proximally-facing surface 148 on the distal side of the O-ring 264. The distal end of the body 170 presents a distally-facing surface 198 on the proximal side of the O-ring 264. A small gap or clearance may exist between the O-ring 264 and the proximally-facing surface 148 of the housing 130 on the distal side of the O-ring 264 and the distally-facing surface 198 of the ultrasonic horn 160 on the proximal side of the O-ring 264. In operation of the ultrasonic handpiece 100, squeezing of the O-ring 264 between the proximally-facing surface 148 of the housing 130 and the distally-facing surface 198 of the ultrasonic horn 160 may serve to limit the amount of distal movement of the ultrasonic horn 160.

On the proximal side of the body 170, the piezoelectric crystals 211, 212, 213, 214 are mounted on the proximal shaft 172 and, in this example, abut against a proximally-facing surface of the body 170. The ultrasonic horn 160 comprises an externally-threaded bolt surface 188 on which an internally-threaded nut 218 is threaded to fasten the set of piezoelectric crystals 210 in place from the proximal side of the set of piezoelectric crystals 210.

On the proximal end 162 of the ultrasonic horn 160, proximal to the bolt surface 188, the ultrasonic horn 160 is resiliently suspended with respect to the housing 130. Thus, the ultrasonic horn 160 can be considered to be free "floating," i.e., resiliently suspended, within the housing 130. In the illustrated example, the proximal end 162 of the ultrasonic horn 160 is resiliently suspended relative to the housing 130 through a resilient elastomeric O-ring 262 that is mounted within the aspiration luer 220, as described below.

Figure 4:
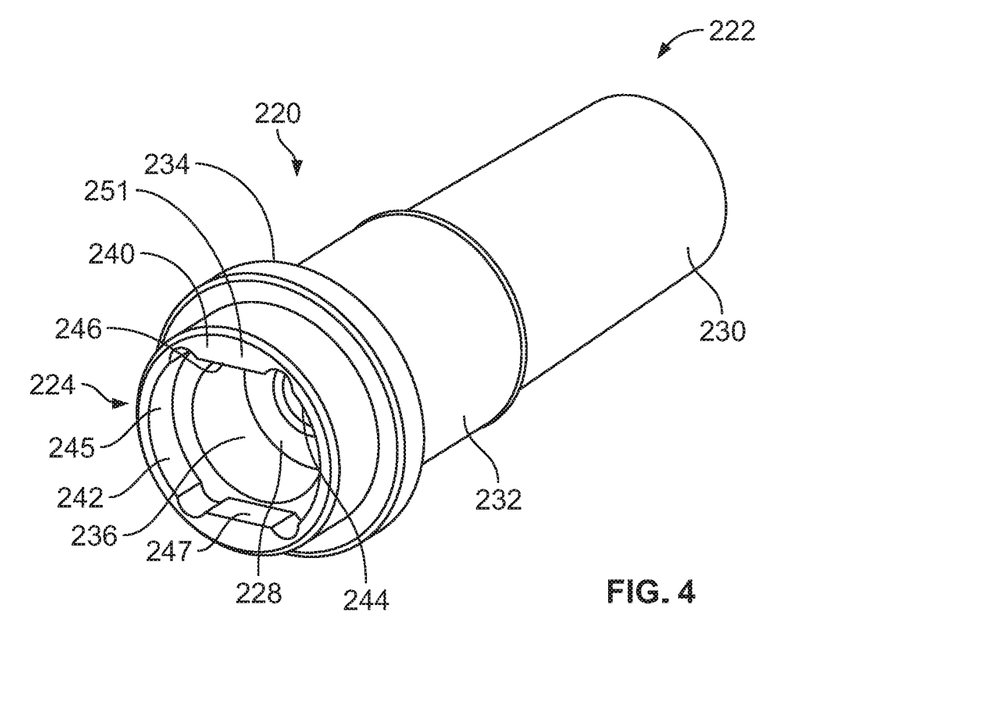
FIG. 4 shows a perspective view of the aspiration luer component of the ultrasonic handpiece of FIG. 1.

FIG. 4 shows a perspective view of the aspiration luer 220 of the ultrasonic handpiece 100 of FIG. 1. The aspiration luer 220 is fixed relative to the housing 130 at the proximal end 132 of the housing 130. The aspiration luer 220 comprises a stem 230 that extends through the port 152 at the proximal end 132 of the housing 130. The aspiration luer 220 further comprises a body 232 that has a diameter larger than the stem 230 and larger than the port 152 so that the body 232 limits proximal movement of the aspiration luer 220 through the port 152 during assembly of the device. The aspiration luer 220 may be rigidly attached to the housing 130 to prevent longitudinal and rotational movement of the aspiration luer 220 relative to the housing 130. This attachment may be accomplished by mechanical structure and/or one or more adhesives.

As illustrated in FIGS. 1 and 2, the ultrasonic handpiece 100 comprises a resilient elastomeric O-ring 262 between the ultrasonic horn 160 and the aspiration luer 220 at the proximal end 162 of the ultrasonic horn 160. The ultrasonic horn 160 comprises an O-ring surface 176 that faces outwardly, and the aspiration luer 220 comprises an O-ring surface 236 that faces inwardly. The O-ring 262 is positioned between the O-ring surface 176 of the ultrasonic horn 160 and the O-ring surface 236 of the aspiration luer 220. The space in which the O-ring 262 is located may also be bounded on proximal and distal sides of the O-ring 262. For example, on the distal side of the O-ring surface 176, the ultrasonic horn 160 may have a larger-diameter portion (e.g., horn key 180 or another portion as shown) that presents a proximally-facing surface on the distal side of the O-ring 262. Similarly, on the proximal side of the O-ring surface 236, the aspiration luer 220 may have a shoulder at a transition of the channel 226 from a first diameter at the proximal end of the channel 226 to a larger diameter at an enlarged portion 228 at the proximal end of the channel 226. The shoulder presents a distally-facing surface on the proximal side of the O-ring 262. A small gap or clearance may exist between the O-ring 262 and the adjacent proximally-facing surface and distally-facing surface.

The suspension of the ultrasonic horn 160 within the aspiration luer 220 through the resilient O-ring 262 provides freedom of movement of the ultrasonic horn 160 relative to the aspiration luer 220. The resilient O-ring 262 at the proximal end 162 of the ultrasonic horn 160 serves as a resilient suspension of the ultrasonic horn 160 within the housing 130. In this way, the ultrasonic handpiece 100 may be described as having a floating ultrasonic horn 160, wherein the proximal end 162 of the ultrasonic horn 160 is free to move relative to the housing 130 and is not rigidly mounted relative to the housing 130.

In some embodiments, it may be desirable to limit the rotational movement of the ultrasonic horn 160 within the housing 130. Such limitation of rotation can be useful, for example, to allow the working tip 110 to be threaded onto the ultrasonic horn 160 by threads 118 and threads 168 while limiting the ultrasonic horn 160 from rotating relative to the housing 130 in a manner that would interfere with attaching the working tip 110.

In the illustrated example, to allow the proximal end 162 of the ultrasonic horn 160 to be free to move relative to the housing 130 while limiting its rotation relative to the housing 130, the proximal end 162 of the ultrasonic horn 160 comprises a horn key 180. The horn key 180 has a structure for coupling with a handpiece key (for example, a handpiece key 240 that is part of the aspiration luer 220) that is fixed relative to the housing 130. In the illustrated example, the coupling of the horn key 180 to the handpiece key (e.g., handpiece key 240) limits rotation of the proximal end 162 of the ultrasonic horn 160 relative to the handpiece key and the housing 130 but does not limit the proximal end 162 of the ultrasonic horn 160 from moving in a longitudinal direction relative to the handpiece key and the housing 130.

As shown in FIGS. 1, 2, and 4, in the illustrated example, the handpiece key 240 is part of the aspiration luer 220 and is located at the distal end 224 of the aspiration luer 220, although other embodiments and locations are possible. As shown in FIGS. 3 and 4, the horn key 180 and the handpiece key 240 are shaped for coupling the ultrasonic horn 160 to the aspiration luer 220 while both allowing the ultrasonic horn 160 to move in a longitudinal direction relative to the aspiration luer 220 and limiting rotation of the ultrasonic horn 160 within the aspiration luer 220. The horn key 180 has a horn key outer surface 182 that corresponds to a handpiece key inner surface 242 of the handpiece key 240. For example, the horn key outer surface 182 may comprise two curved surfaces 184, 185 and two flat surfaces 186, 187, and the handpiece key inner surface 242 may comprise two curved surfaces 244, 245 and two flat surfaces 246, 247. When the device is assembled and the horn key 180 is coupled to the handpiece key 240, the curved surface 184 is adjacent the curved surface 244, the curved surface 185 is adjacent the curved surface 245, the flat surface 186 is adjacent the flat surface 246, and the flat surface 187 is adjacent the flat surface 247. Many other configurations are possible within the scope of enabling the proximal end of the ultrasonic horn 160 to be free to move relative to the housing 130 while limiting rotation of the ultrasonic horn 160.

The horn key 180 and corresponding handpiece key 240 may have some clearance between them to allow some play and some limited rotational movement of the ultrasonic horn 160 relative to the aspiration luer 220. That is, the ability of the proximal end 162 of the ultrasonic horn 160 to rotate relative to the handpiece key 240 and the housing 130 may be allowed to some limited extent but is limited by the horn key 180 and handpiece key 240. Thus, the proximal end 162 of the ultrasonic horn 160 is free to move in the longitudinal direction relative to the housing 130 while the ability of the proximal end 162 of the ultrasonic horn 160 to rotate relative to the housing 130 may be limited.

The extent of longitudinal movement of the proximal end 162 of the ultrasonic horn 160 relative to the housing 130 may also be limited. For example, the ultrasonic handpiece 100 may have a dead stop which prevents or limits the extent of longitudinal movement of the ultrasonic horn 160 in the proximal direction. As one possible stop, the ultrasonic horn 160 may have a proximally-facing horn stop surface 191 that abuts against a distally-facing handpiece stop surface 251, which prevents or stops proximal movement of the ultrasonic horn 160. Thus, the handpiece stop surface 251 is adapted to cooperate with the horn stop surface 191 to prevent or limit an extent of longitudinal motion of the ultrasonic horn 160 in the proximal direction. In the illustrated example, the distally-facing handpiece stop surface 251 is part of the aspiration luer 220. Alternatively, it may be part of the housing 130 or part of another component rigidly attached to the housing. The extent of distal movement of the ultrasonic horn 160 may similarly be limited.

At its distal end 224, the aspiration luer 220 may include additional structure as shown. For example, the aspiration luer 220 may include a ring 234. The ring 234 may serve as a stop surface for a washer 216 that is placed around the distal end 224 of the aspiration luer 220.

The disclosure herein of an ultrasonic horn that is flexibly suspended or floating at its proximal end and/or an ultrasonic horn that is flexibly suspended or floating at its proximal end and its nodal region with no rigid attachment or fixation points provides advantages over the prior art. The use of a floating ultrasonic horn 160 as described herein enables the use of a shorter ultrasonic horn 160, as described below. This in turn enables the use of a pumping module 290 located at the proximal end of the ultrasonic handpiece 100. The pumping module 290 may be attached to the proximal end of the housing 130, as shown in FIG. 1. The shorter ultrasonic horn 160 enables the use of a shorter housing 130 which allows the inclusion of the pumping module 290 while still maintaining an overall length of the ultrasonic handpiece 100 that is small enough so that it can be handled easily by the operator.

Figure 5:
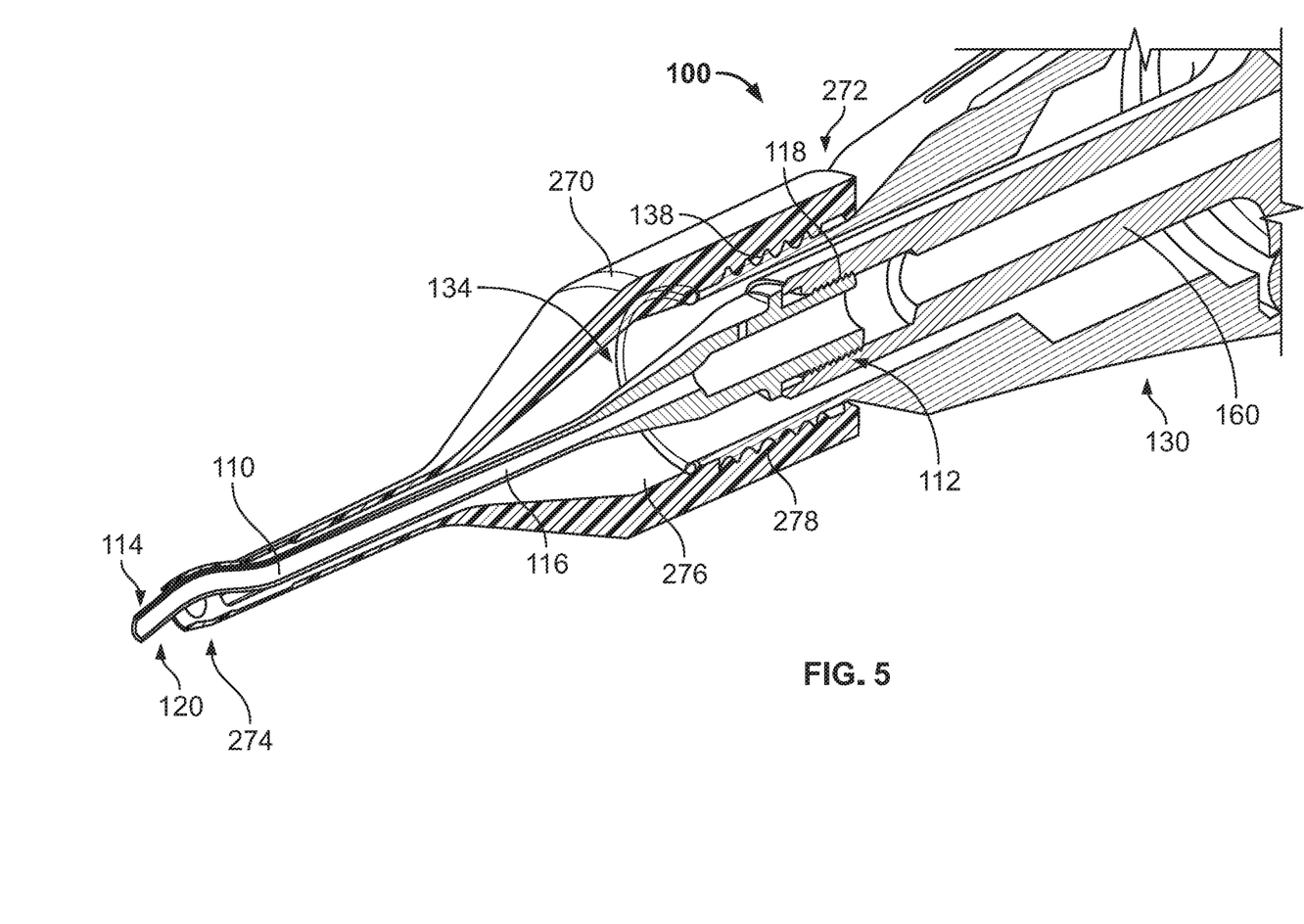
FIG. 5 shows a perspective view in cross-section of the distal end of the ultrasonic handpiece of FIG. 1 with an irrigation sleeve in place.

FIG. 5 shows a perspective view in cross-section of the distal end of the ultrasonic handpiece 100 of FIG. 1 with an irrigation sleeve 270 in place. The irrigation sleeve 270 serves to direct an irrigation fluid, e.g., saline, to the distal end 114 of the working tip 110. The housing 130 has an irrigation supply line 268 through which an irrigation fluid may be introduced. The housing 130 has external threads 138 at its distal end 134, and the irrigation sleeve 270 has internal threads 278 at its proximal end 272 by which the irrigation sleeve 270 may be attached to the housing 130. The irrigation sleeve 270 is positioned around the working tip 110 to provide a fluid passageway or channel 276 from the position of its attachment to the housing 130 through the space between the irrigation sleeve 270 and the working tip 110. The irrigation sleeve 270 has an opening at its distal end 274 adjacent the opening at the distal end 114 of the working tip 110. When an irrigation fluid is introduced through the supply line 268 in the housing 130, it passes through the channel 276 of the irrigation sleeve 270 and out of the opening at the distal end 274 of the irrigation sleeve 270.

Figure 6:
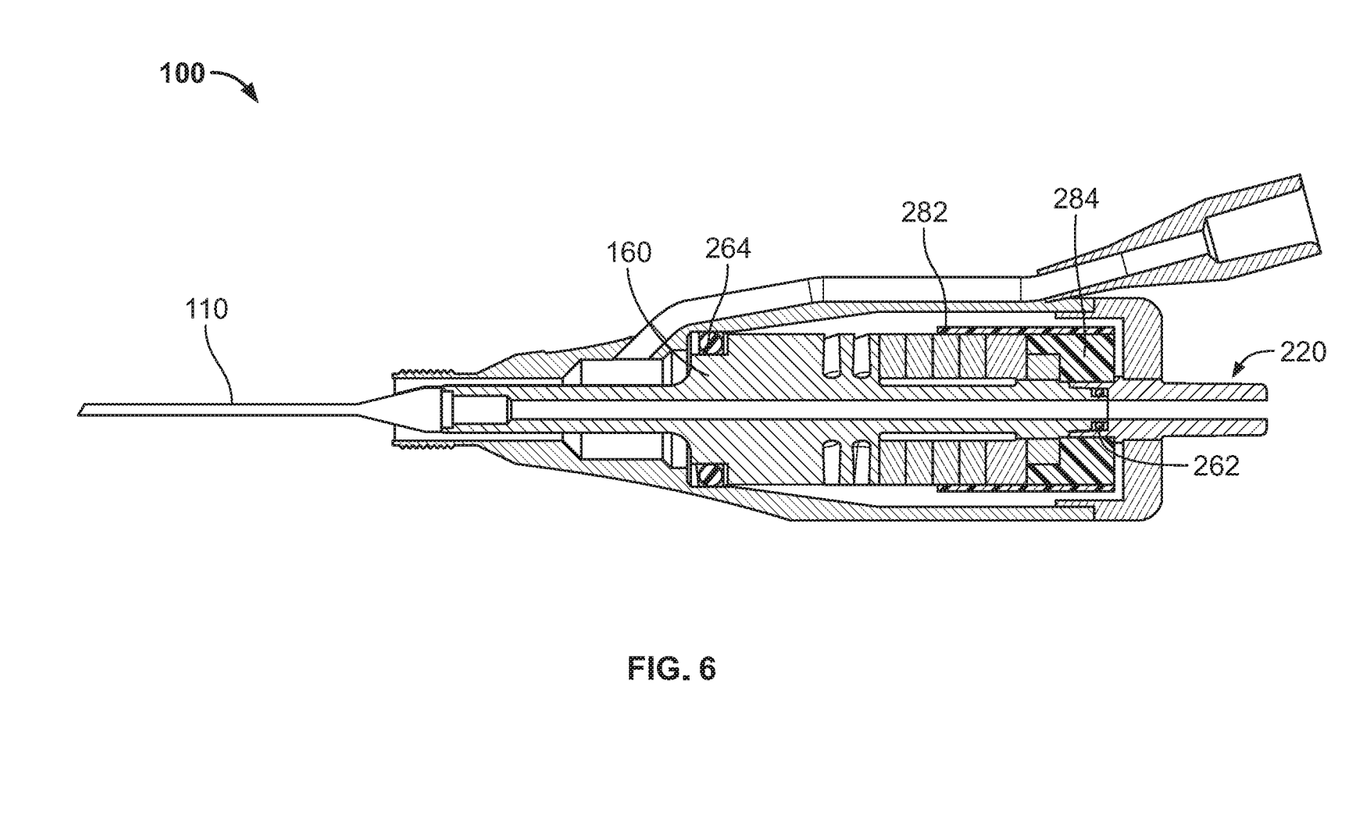
FIG. 6 shows another cross-sectional view of the ultrasonic handpiece of FIG. 1.

FIG. 6 shows another cross-sectional view of the ultrasonic handpiece 100 of FIG. 1. As can be seen in FIG. 6, an elastomeric potting compound 284 such as a silicone adhesive may be introduced into the space around the coupling of the ultrasonic horn 160 to the aspiration luer 220. An elastomeric sleeve 282 such as a silicone sleeve may be positioned on the outside of the set of piezoelectric crystals 210 and may serve as an outer boundary for the elastomeric potting compound 284. The elastomeric potting compound 284 and elastomeric sleeve 282 may help keep components in place while facilitating resilient suspension of the ultrasonic horn 160 and allowing its freedom of movement as described above.

For operation, the ultrasonic handpiece 100 may be connected to a control console. For example, the ultrasonic handpiece 100 may be connected to a control console like the control console of the CENTURION® Vision System of Alcon, headquartered in Fort Worth, Texas. The ultrasonic handpiece 100 may be connected to the control console by one or more electric cables, for example one or more electric cables that are used for supplying current to the set of piezoelectric crystals 210. The ultrasonic handpiece 100 may also be connected to the control console by one or more tubes, for example one or more tubes that may supply an irrigation fluid from the control console to the proximal end of the irrigation supply line 268 of the housing 130.

In operation of the device, the operator positions the working end 120 of the working tip 110 at a desired location, such as adjacent a cataractous lens of a patient. Irrigation fluid such as saline may be supplied from the control console through the irrigation supply line 268 and irrigation sleeve 270. The set of piezoelectric crystals 210 may be activated by supplying electrical current from the control console to electrical wiring 215 that connects to the set of piezoelectric crystals 210. The activation of the piezoelectric crystals 210 induces vibration of the ultrasonic horn 160. The ultrasonic horn 160 may have one or more helical grooves 192 in order to introduce a torsional movement to the vibration. The vibration of the ultrasonic horn 160 causes vibration of the attached working tip 110, which can break up or phacoemulsify the desired tissue such as the cataractous lens. At the same time, the pumping module 290 may be used to apply suction at the proximal end 222 of the aspiration luer 220 and through the aspiration channel 280 comprising channel 226 of the aspiration luer 220, channel 166 of the ultrasonic horn 160, and channel 116 of the working tip 110, thereby suctioning away fluid and tissue and/or lens fragments that have been separated by the action of the working tip 110.

In use of the ultrasonic handpiece 100, the maximum vibrations are located at, or are approximately adjacent to, the distal end 114 of the working tip 110. The ultrasonic horn 160 may have little or no amplitude of vibration at, or approximately adjacent to, the single nodal region 200. The proximal end 162 of the ultrasonic horn 160 is free to move relative to the housing 130 as described above. Thus, in use, the ultrasonic horn 160 vibrates the working tip 110, and the proximal end 162 of the ultrasonic horn 160 moves relative to the housing 130, as it is free to do on account of its resilient or flexible suspension.

The use of an ultrasonic horn 160 that has a floating or flexibly suspended proximal end 162 facilitates the use of an ultrasonic horn with a single nodal region 200. In typical prior art devices, the proximal end of ultrasonic horn is rigidly attached to the housing (directly or indirectly), such as by a bolt connection, and has a nodal region at the area of this rigid attachment. With an ultrasonic horn 160 that has a floating or flexibly suspended proximal end 162 as described herein, the proximal end 162 need not be a nodal region. Thus, the proximal end 162 is free to vibrate as shown. If a vibrating, non-nodal proximal end of an ultrasonic horn were rigidly attached to the housing, or to one or more other components rigidly attached to the housing, the attachment could cause undesirable adverse consequences, such as resonance dampening, generation of excessive heat, and/or unwanted vibration of the housing.

With an ultrasonic horn 160 that has a floating or flexibly suspended proximal end 162 and/or that is floating or flexibly suspended at its proximal end 162 and its single nodal region 200 with no rigid fixation points as described herein, unwanted resonance dampening, generation of excessive heat, and/or unwanted vibration of the housing can be avoided. In addition, a shorter ultrasonic horn 160 can be employed, because its length needs only the single central nodal region 200. As an example, an ultrasonic horn as described herein can be approximately 1.5 inches in length, or less than 2 inches in length, shorter than typical ultrasonic horns which can be, for example, 4 inches in length or more.

The use of a shorter ultrasonic horn 160 enables the use of a shorter housing 130, which in turn enables the attachment of a pumping module 290 at the proximal end 132 of the housing 130 while maintaining a desirable ergonomic assembly length and without resulting in an ultrasonic handpiece that is too long to be easily handled by the operator. Placing a pumping module 290 at the proximal end of the ultrasonic handpiece 100 means that the distance between the suction pump and the distal end 114 of the working tip 110 is reduced. In typical prior devices, the suction pump is located at the control console and connected to the handpiece by long tubing, which may be, for example, six feet in length. With a pumping module 290 at the proximal end of the ultrasonic handpiece 100 as described herein, the connection between the suction pump and the distal end 114 of the working tip is only a few inches of rigid channel length. This results in a better vacuum and improves chamber stability. For example, in the prior art, if there is an occlusion in the line that suddenly clears under heavy vacuum, a large surge in suction can occur, which can be potentially damaging. With a pumping module 290 at the proximal end of the ultrasonic handpiece 100 as described herein, the potential for occlusion is reduced, and, moreover, there is less potential for a sudden surge in heavy vacuum suction upon release of an occlusion.

As persons having ordinary skill in the art will appreciate, the systems and methods as disclosed herein have a number of advantages over prior systems and methods. Such advantages include shorter handpieces, the ability to include a pumping module as part of the handpiece while maintaining an ergonomically desirable design, avoidance of resonance dampening, reduced heat generation, reduced vibration, reduced risk of occlusion, more stable vacuum pressure, improved chamber stability, lower cost, and/or improved patient outcome.

Persons of ordinary skill in the art will appreciate that the implementations encompassed by the disclosure are not limited to the particular exemplary implementations described above. In that regard, although illustrative implementations have been shown and described, a wide range of modification, change, and substitution is contemplated in the foregoing disclosure. It is understood that such variations may be made to the foregoing without departing from the scope of the disclosure. Accordingly, it is appropriate that the appended claims be construed broadly and in a manner consistent with the disclosure.

What is claimed is:

1. An ultrasonic handpiece comprising:
    a housing comprising a proximal end and a distal end;
    a working tip extending from the distal end of the housing;
    a crystal and horn assembly positioned within the housing, the crystal and horn assembly comprising an ultrasonic horn and a set of piezoelectric crystals that induce vibration of the ultrasonic horn, the ultrasonic horn comprising a proximal end and a distal end, the working tip connected to the distal end of the ultrasonic horn,
        wherein an outer surface of the crystal and horn assembly and an inner surface of the housing at least partially define a hollow chamber within the housing,
        wherein the ultrasonic horn comprises a plurality of helical grooves configured to introduce torsional movement during vibration of the ultrasonic horn, and
        wherein the proximal end of the ultrasonic horn is free to move longitudinally relative to the housing; and
    an aspiration luer at least partially disposed through the hollow chamber of the housing and proximal to the set of piezoelectric crystals, wherein:
        the aspiration luer is configured to facilitate aspiration through the housing, and
        the aspiration luer comprises one or more surfaces configured to directly contact the ultrasonic horn and limit an ability of the proximal end of the ultrasonic horn to rotate relative to the housing.
2. The ultrasonic handpiece of claim 1, wherein the ultrasonic horn is resiliently suspended within the housing.

3. The ultrasonic handpiece of claim 2, wherein the proximal end of the ultrasonic horn is resiliently suspended within the housing by a resilient ring.
4. The ultrasonic handpiece of claim 3, wherein:
    the aspiration luer is fixed relative to the housing at the proximal end of the housing, and
    the resilient ring by which the proximal end of the ultrasonic horn is resiliently suspended is located between the ultrasonic horn and the aspiration luer.
5. The ultrasonic handpiece of claim 1, wherein in operation the ultrasonic horn has a single nodal region, the single nodal region being located between the proximal end and the distal end of the ultrasonic horn.
6. The ultrasonic handpiece of claim 5, wherein the single nodal region of the ultrasonic horn is resiliently suspended within the housing by a resilient ring positioned between the housing and the ultrasonic horn at the single nodal region.
7. The ultrasonic handpiece of claim 5, wherein the ultrasonic horn has a longitudinal axis extending in a longitudinal direction, and wherein the ability of the proximal end of the ultrasonic horn to rotate about the longitudinal axis is limited.
8. The ultrasonic handpiece of claim 7, wherein:
    the ultrasonic horn comprises a horn key located at the proximal end of the ultrasonic horn,
    the aspiration luer comprises a handpiece key at a distal end of the aspiration luer that is fixed relative to the housing,
    the handpiece key comprises the one or more surfaces, the one or more surfaces comprising two opposing curved surfaces joined by two opposing flat surfaces,
    the horn key is coupled to the handpiece key, and
    the ability of the proximal end of the ultrasonic horn to rotate relative to the housing is limited by the coupling of the horn key to the handpiece key.
9. The ultrasonic handpiece of claim 1, wherein the ultrasonic horn further comprises a horn stop surface, wherein the horn stop surface limits an extent of longitudinal motion of the ultrasonic horn in a proximal direction.
10. The ultrasonic handpiece of claim 9, further comprising a handpiece stop surface, wherein the handpiece stop surface is adapted to cooperate with the horn stop surface to limit an extent of longitudinal motion of the ultrasonic horn in the proximal direction.
11. The ultrasonic handpiece of claim 10, wherein:
    the aspiration luer is fixed relative to the housing at the proximal end of the housing, and
    the handpiece stop surface is part of the aspiration luer.
12. The ultrasonic handpiece of claim 1, further comprising a pumping module located at the proximal end of the handpiece.
13. The ultrasonic handpiece of claim 1, wherein in operation the ultrasonic horn vibrates with a single nodal region, the single nodal region being located between the proximal end and the distal end of the ultrasonic horn, and wherein a maximum amplitude of vibration is at a distal end of the working tip.
14. A method of using an ultrasonic handpiece, comprising:
    activating an ultrasonic handpiece, the ultrasonic handpiece comprising:
        a housing comprising a proximal end and a distal end;
        a working tip extending from the distal end of the housing;
        a crystal and horn assembly positioned within the housing, the crystal and horn assembly comprising an ultrasonic horn and a set of piezoelectric crystals that induce vibration of the ultrasonic horn, the ultrasonic horn comprising a proximal end and a distal end, the working tip connected to the distal end of the ultrasonic horn,
- wherein an outer surface of the crystal and horn assembly and an inner surface of the housing at least partially define a hollow chamber within the housing, and
- wherein the ultrasonic horn comprises a plurality of helical grooves configured to introduce torsional movement during vibration of the ultrasonic horn; and an aspiration luer at least partially disposed through the hollow chamber of the housing proximal to the set of piezoelectric crystals, wherein:
- the aspiration luer is configured to facilitate aspiration through the housing, and
- the aspiration luer comprises a plurality of surfaces configured to directly contact the ultrasonic horn and limit an ability of the proximal end of the ultrasonic horn to rotate relative to the housing, the plurality of surfaces comprising two opposing curved surfaces joined by two opposing flat surfaces; and vibrating the ultrasonic horn such that the working tip is vibrated and such that the proximal end of the ultrasonic horn moves relative to the housing.

15. The method of claim 14, wherein the ultrasonic horn is resiliently suspended within the housing.

16. The method of claim 14, wherein in the step of vibrating the ultrasonic horn, the ultrasonic horn has a single nodal region, the single nodal region being located between the proximal end and the distal end of the ultrasonic horn.

17. The method of claim 14, wherein the ultrasonic horn has a longitudinal axis extending in a longitudinal direction, and wherein in the step of vibrating the ultrasonic horn, the proximal end of the ultrasonic horn moves in the longitudinal direction relative to the housing.

18. The method of claim 14, wherein the ultrasonic handpiece further comprises a pumping module located at the proximal end of the handpiece.

19. A system for performing operations with an ultrasonic handpiece, the system comprising:
- an ultrasonic handpiece comprising a housing comprising a proximal end and a distal end;
- a working tip extending from the distal end of the housing;
- a crystal and horn assembly positioned within the housing, the crystal and horn assembly comprising an ultrasonic horn and a set of piezoelectric crystals that induce vibration of the ultrasonic horn, the ultrasonic horn comprising a proximal end and a distal end, the working tip connected to the distal end of the ultrasonic horn,
  - wherein an outer surface of the crystal and horn assembly and an inner surface of the housing at least partially define a hollow chamber within the housing, and
  - wherein the ultrasonic horn comprises a plurality of helical grooves configured to introduce torsional movement during vibration of the ultrasonic horn; and
- an aspiration luer at least partially disposed through the hollow chamber of the housing proximal to the set of piezoelectric crystals, wherein:
  - the aspiration luer is configured to facilitate aspiration through the housing, and
  - the aspiration luer comprises a plurality of surfaces configured to directly contact the ultrasonic horn and limit an ability of the proximal end of the ultrasonic horn to rotate relative to the housing, the plurality of surfaces comprising two opposing curved surfaces joined by two opposing flat surfaces; and
- a control console for controlling operations of the ultrasonic handpiece; and
- at least one electrical connection between the control console and the ultrasonic handpiece for activating the set of piezoelectric crystals,
  - wherein the proximal end of the ultrasonic horn is free to move longitudinally relative to the housing.

* * * * *